United States Patent [19]

Bradshaw et al.

[11] 4,160,036

[45] Jul. 3, 1979

[54] 4-HYDROXY-1,3-BENZENEDIMETHANOL DERIVATIVES

[75] Inventors: John Bradshaw; Ian Collins, both of Ware, England

[73] Assignee: Allen & Hanburys Limited, London, England

[21] Appl. No.: 881,658

[22] Filed: Feb. 27, 1978

Related U.S. Application Data

[63] Continuation of Ser. No. 709,926, Jul. 29, 1976, abandoned.

[30] Foreign Application Priority Data

Jul. 29, 1975 [GB] United Kingdom ............... 31678/75

[51] Int. Cl.$^2$ ..................... A01N 9/20; A01N 9/24; C07C 91/22
[52] U.S. Cl. .................... 424/330; 260/340.7; 260/501.18; 260/501.19; 260/562 P; 260/566 D; 260/566 F; 260/570.5 C; 260/570.6; 260/570.8 R; 260/577; 260/592; 260/599; 424/316; 424/324; 560/19; 560/37; 560/45
[58] Field of Search ...................... 260/501.18, 501.19, 260/570.6, 562 P; 424/316, 324, 330

[56] References Cited

U.S. PATENT DOCUMENTS

| | | | |
|---|---|---|---|
| 3,135,797 | 6/1964 | Biel ..................................... | 260/570.6 |
| 3,284,468 | 11/1966 | Keller ............................. | 260/570.6 X |
| 3,644,353 | 2/1972 | Lunts et al. .................... | 260/570.6 X |
| 3,879,442 | 4/1975 | Schwender et al. ........... | 260/570.6 X |

*Primary Examiner*—Robert V. Hines
*Attorney, Agent, or Firm*—Bacon & Thomas

[57] ABSTRACT

Compounds of the general formula (I):

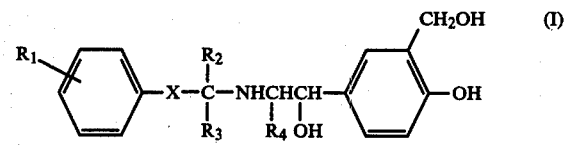

in which one or more substituents $R_1$ may be present and in which:

$R_1$ represents a halogen atom, preferably fluorine or chlorine, or a trifluoromethyl group or a group $-NR_5R_6$ in which $R_5$ and $R_6$ which may be the same or different represent a hydrogen atom, or an alkyl group containing from 1 to 6 carbon atoms, preferably 1 to 4 carbon atoms or an acyl group, preferably the residue of a $C_1$-$C_6$ alkanoic acid;

X represents a straight or branched chain alkyl group containing 2 to 6 carbon atoms; and $R_2$ and $R_3$ which may be the same or different each represent a hydrogen atom or an alkyl group containing from 1 to 4 carbon atoms, preferably a methyl group; and $R_4$ represents a hydrogen atom or an alkyl group containing 1 to 4 carbon atoms, are provided together with processes for the production thereof. They have a $\beta_2$-stimulant activity.

23 Claims, No Drawings

4-HYDROXY-1,3-BENZENEDIMETHANOL DERIVATIVES

This is a continuation of application Ser. No. 709,926, filed July 29, 1976, now abandoned.

This invention relates to new compounds having a stimulant activity on $\beta_2$-adrenoreceptors and to processes for their production.

According to the invention there are provided, as new compounds, compounds of the general formula (I):

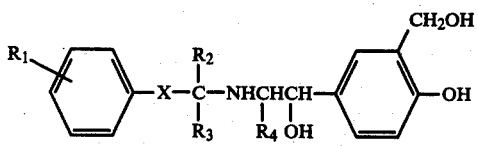

in which one or more substituents $R_1$ may be present and in which:

$R_1$ represents a halogen atom, preferably fluorine or chlorine, or a trifluoromethyl group or a group $-NR_5R_6$ in which $R_5$ and $R_6$ which may be the same or different represent a hydrogen atom, or an alkyl group containing from 1 to 6 carbon atoms, preferably 1 to 4 carbon atoms or an acyl group, preferably the residue of a $C_1$–$C_6$ alkanoic acid;

X represents a straight or branched chain alkylene group containing 2 to 6 carbon atoms in which at least two of the carbon atoms are in the straight chain of carbon atoms leading to the group

and $R_2$ and $R_3$ which may be the same or different each represent a hydrogen atom or an alkyl group containing from 1 to 4 carbon atoms, preferably a methyl group; and $R_4$ represents a hydrogen atom or an alkyl group containing 1 to 4 carbon atoms.

In one aspect of the invention those compounds which are preferred are those in which:

$R_1$ represents halogen, in particular chlorine or fluorine, dialkylamino, preferably dimethylamino, alkylamino, preferably ethylamino, acylamino, preferably acetylamino and trifluoromethyl;

X represents the group $-(CH_2)_n$, where n represents 2, 3 or 4 or represents a group $-CH_2-C(CH_3)_2$ or $-C(CH_3)_2-CH_2-$;

$R_2$ and $R_3$ both represent hydrogen or alkyl in particular methyl or ethyl; and $R_4$ represents hydrogen or alkyl, preferably methyl.

In another aspect of the invention, preferred meanings for $R_1$ are as follows:

Halogen, preferably chlorine or fluorine, and dialkylamino, preferably dimethylamino. Preferably these groups $R_1$ are in the para position although when $R_1$ is a fluorine atom this may be in the ortho or meta position. X preferably represents $-(CH_2)_n$, where n=2 or 3. Prerably $R_2$ and $R_3$ are hydrogen, or alkyl preferably methyl and $R_4$ preferably represents hydrogen.

Specific preferred meanings for the group

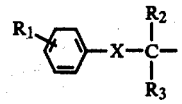

are as follows:

3-(4-fluorophenyl)-1-methylpropyl
3-(4-chlorophenyl)-1-methylpropyl
3-(4-dimethylaminophenyl)-1-methylpropyl
3-(2-fluorophenyl)-1-methylpropyl
3-(3-fluorophenyl)-1-methylpropyl
3-(4-fluorophenyl)propyl
3-(4-fluorophenyl)-1,1-dimethylpropyl
3-(4-trifluoromethyl)-1-methylpropyl
4-(4-fluorophenyl)-1-methylbutyl We have found that the compounds of formula (I) as well as their pharmaceutically acceptable salts differ from known selective $\beta_2$-adrenoreceptor stimulants in that they are more active on respiratory smooth muscle than on skeletal muscle, and thus they act as bronchodilators at doses that minimize the undesired effects of tremor.

The relative selectivity of action of the compounds of formula (I) on respiratory smooth muscle as opposed to skeletal muscle is clearly demonstrated in the anaesthetised cat which had undergone a bilateral vagotomy. The compound is injected through a cannulated jugular vein and the effects on respiratory smooth muscle, skeletal muscle, blood pressure and heart rate are measured simultaneously.

The $\beta$-stimulant activity on respiratory smooth muscle was assessed by measuring the effect of the compounds in preventing increases in airways pressure induced by 5-hydroxytryptamine. Airways pressure was measured using a modification of the Dixon and Brodie technique (J. Physiology, 31, 97–173, 1903).

The $\beta$-stimulant activity on skeletal muscle was assessed by measuring the effect of the compounds in decreasing tension on the left soleus muscle developed during the sub-maximal tetanus. The procedure is described by Bowman and Nott, Br. J. Pharmac., 38, 37–49, 1970.

Blood pressure was monitored from a common carotid artery and the heart rate measured by an instantaneous ratemeter triggered by the pulse pressure.

(−) Isoprenaline was used as the reference compound in all the experiments.

The compounds of the invention are also effective as inhibitors of gastric acid secretion.

The compounds according to the invention contain asymmetric centres, and the invention covers all possible diastereoisomers and enantiomers.

The invention also extends to pharmaceutically acceptable salts of the compounds of formula (I). Such salts include acid addition salts for example salts with inorganic acids such as hydrochlorides and sulphates, and salts with organic acids, such as acetates. Other salts include salts with alkali metals, e.g. sodium salts.

The compounds of formula (I) may be prepared by a number of processes and Examples of such processes are given below.

(1) The compounds of formula (I) above may be prepared by reducing a compound of formula (II):

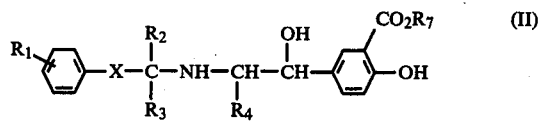 (II)

in which $R_1$, $R_2$, $R_3$, $R_4$ and X have the meanings given above and $R_7$ represents an alkyl group containing 1 to 4 carbon atoms, with a reducing agent, such as a complex metal hydride, for example lithium aluminium hydride or sodium dihydro bis-(2-methoxyethoxy)aluminate in an aprotic solvent, such as an ether for example diethyl ether, dioxan, tetrahydrofuran or diethylene glycol dimethyl ether or a hydrocarbon such as benzene, or calcium or lithium or sodium borohydride in a suitable solvent, such as a lower alkanol, for example ethanol.

The compound of formula (II) above may be prepared by reductive alkylation of an amine of formula (IV) with a ketone or aldehyde of formula (III):

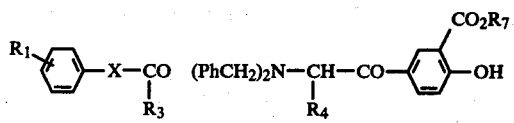

(III)   (IV)

in which $R_1$, $R_3$, $R_4$, X and $R_7$ have the meaning given above, with hydrogen in the presence of a catalyst, for example a noble metal catalyst, such as palladium, platinum or mixtures thereof, in the presence of a solvent, such as an alkanol, preferably ethanol. In place of compound of formula (IV) the corresponding amino secondary alcohol (IVa):

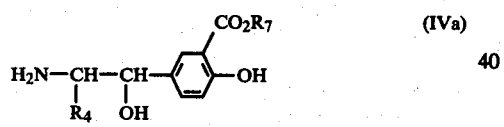 (IVa)

may be reductively alkylated with a compound of formula (III) in the presence of a reducing agent, such as a complex metal hydride, in particular sodium cyanoborohydride.

(2) The compounds of formula (I) may also be prepared by reductive alkylation of an amine of formula (V):

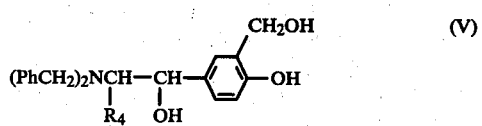 (V)

in which $R_4$ has the meaning given above, with a ketone or aldehyde of formula (III), in which $R_1$ and $R_3$ have the meanings defined above, with hydrogen in the presence of a catalyst, for example a noble metal catalyst, such as palladium and platinum or mixtures thereof, in a solvent, such as an alkanol, preferably ethanol. In place of the compound of formula (V) the corresponding α-aminoketone may be used.

(3) The compounds of formula (I) may also be prepared by reductive alkylation of an amine of formula (VI):

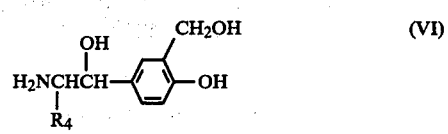 (VI)

in which $R_4$ has the meaning given above, with a ketone or aldehyde of formula (III) by a catalytic hydrogenation procedure as described in (1) or (2) or by use of a reducing agent such as complex metal hydride, in particular sodium or potassium borohydride, in a solvent such as an alkanol, preferably methanol or ethanol. This process is related to that of (2) above since the compound of formula (VI) may be prepared by the debenzylation of the compound of formula (V) for example with hydrogen in the presence of a noble metal catalyst. In these processes the phenolic groups in compounds (V) and (VI) may be protected for example as esters or ethers such as an acetate or a benzyl ether which groups may be subsequently removed by treatment with for example acid or by catalytic hydrogenation procedures.

(4) The compounds of formula (I) where $R_4$ is hydrogen may also be prepared by reacting an amine of formula (VII) with a phenyl glyoxal of formula (VIII):

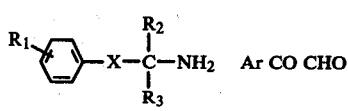

(VII)   (VIII)

in which $R_1$, $R_2$, $R_3$ and X have the meanings given above and Ar represents the group:

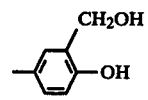

or a group convertible thereto for example a group of the formula:

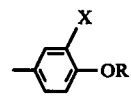

in which X represents a group $CO_2R_7$ in which $R_7$ represents an alkyl group and R represents an aralkyl group preferably a benzyl group in a solvent such as an alkanol preferably ethanol, with subsequent reduction of the resultant imine with for example a complex metal hydride, or hydrogen and a noble metal catalyst. If necessary the ester group $CO_2R_7$ may be converted to the group —$CH_2OH$ as part of the reduction process utilising the complex metal hydride or at any convenient stage. Where R is a benzyl group then this may be removed in a separate hydrogenation step or as part of the imine reduction step.

(5) The compounds of formula (I) where $R_4$ is hydrogen may also be prepared by reacting an amine of formula (VII) with an epoxide of formula (IX) or a halohydrin of formula (X):

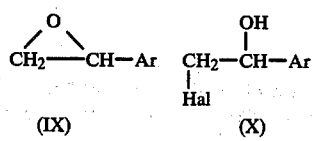

(IX)   (X)

in which Ar represents the group:

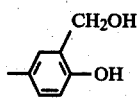

or a group convertible thereto and Hal represents a halogen atom, in a solvent such as a hydrocarbon, for example toluene, or an alkanol, such as ethanol.

In connection with this process the group convertible to Ar may be a group of the formula:

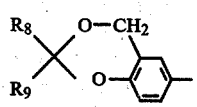

in which $R_8$ and $R_9$ may be the same or different and represent a straight or branched chain $C_{1-4}$ alkyl group or $R_8$ and $R_9$ together form a methylene chain $-(CH_2)_n-$ wherein n is 3 to 5. As a final stage in the process this group is converted into a group Ar by treatment with a suitable acid.

(6) The compounds of the invention where $R_2$ is hydrogen may also be prepared by the hydrogenation of the derivative of formula (XI):

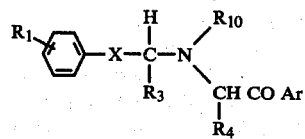

in which $R_1$, $R_3$, $R_4$, X, and Ar have the meanings given and $R_{10}$ represents hydrogen or benzyl in the presence of a catalyst for example a noble metal catalyst, such as platinum, palladium or mixtures thereof, in a solvent such as an alkanol, for example ethanol.

The compounds of formula (XI) may be prepared by the condensation of the amine of formula (XII) with a halo ketone of formula (XIII):

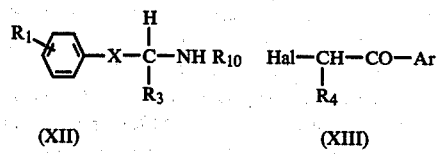

in which $R_1$, $R_3$, X, Hal, Ar and $R_{10}$ have the meanings given above, in a solvent such as a hydrocarbon, for example toluene, a ketone, such as methyl ethyl ketone, an alkanol, such as ethanol or a halogenated hydrocarbon, such as chloroform.

(7) In another process one may reduce an intermediate of the formula (XIV):

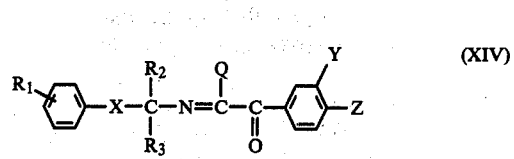

in which $R_1$, $R_2$, $R_3$ and X have the above stated meaning, Q represents halogen and Y and Z are groups convertible to $-CH_2OH$ and $-OH$ respectively. This reduction may be effected with diborane or a complex metal hydride such as lithium aluminium hydride. The compound of formula (XIV) may be prepared by the condensation of a benzoyl halide with an appropriate isocyanide.

(8) The compounds of formula (I) may also be prepared by hydroxymethylation of a compound of formula (XV):

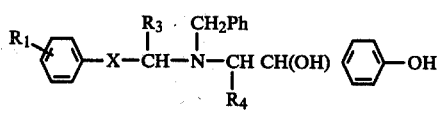

in which $R_1$, $R_3$, $R_4$ and X have the meanings defined above, with formaldehyde or a formaldehyde yielding compound in the presence of a strong base and an alkali metal borate, with subsequent debenzylation.

In carrying out the reaction formaldehyde itself or any suitable source of formaldehyde such as paraformaldehyde may be used. An aqueous solution of formaldehyde, for example 40% Formalin is preferred. The reaction is carried out in the presence of a strong base, preferably an alkali metal hydroxide such as sodium hydroxide, and an alkali metal borate, in particular sodium borate. The reaction is preferably carried out at ambient temperature.

(9) The compounds of formula (I) where $R_2$ is hydrogen may also be prepared by chloromethylation of a compound of formula (XVI):

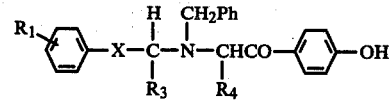

in which $R_1$, $R_3$, $R_4$ and X have the meanings defined above, with formaldehyde and hydrochloric acid, preferably at room temperature. The resultant chloromethyl derivative of formula (XVII):

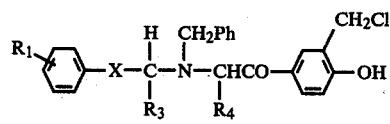

is then hydrolysed with water, preferably with heating to the hydroxymethyl derivative (XVIII):

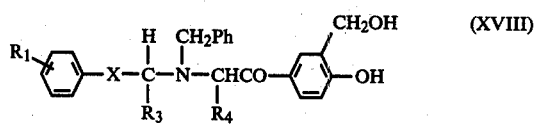

Reduction of this compound with a suitable reducing agent, for example a complex metal hydride, such as sodium borohydride followed by the subsequent removal of the N-benzyl group gives the compound of formula (I).

The compounds according to the invention may be converted to other compounds according to the invention by conversion for example of one group $R_1$ into another group $R_1$ within the meanings given. Thus, $R_1$=N-acyl may be converted into $R_1$=N-alkyl by reduction with a complex metal hydride as described in Example 16.

The invention also provides pharmaceutical compositions which are characterised in that they contain a compound according to the invention, preferably in association with a pharmaceutically acceptable carrier or diluent. The compositions may include, for example, solid or liquid preparations for oral use, or may be in the form of suppositories, injections or in a form suitable for administration by inhalation.

Oral administration is most convenient in the form of tablets which may be prepared according to conventional methods, and may be coated if required. Soluble tablets suitable for sublingual administration may also be used.

Injections may be formulated with the aid of physiologically acceptable carriers and agents as solutions, suspensions or as dry products for reconstitution before use.

For administration by inhalation the compositions according to the invention can be in the form of a metered dose inhalation aerosol, a solution or suspension suitable for nebulisation by mechanical means, or as a cartridge from which the powdered composition may be inhaled with the aid of a suitable device.

The dosage at which the active ingredients are administered may vary within a wide range. A suitable per diem dosage range for systemic use is generally from 1 to 100 mg. The pharmaceutical compositions may with advantage be formulated to provide a dose within this range either as a single unit or a number of units.

In the use of an aerosol for bronchodilatation the dosage unit may be determined by providing a metering valve in the aerosol pack so that it delivers a metered amount on use. Such a metered amount may be of the order of 50–1000 µg.

The following Examples illustrate the invention:

EXAMPLE 1

$\alpha^1$-[[[3-(4-Fluorophenyl)-1-methylpropyl]amino]methyl]-4-hydroxy-1,3-benzenedimethanol (a)

5-[2-[[3-(4-Fluorophenyl)-1-methylpropyl]amino]-1-hydroxyethyl]-2-hydroxybenzoic acid, methyl ester, hydrochloride 2-Hydroxy-5-[[bis(phenylmethyl)amino]acetyl]benzoic acid, methyl ester, hydrochloride (8.52 g) was treated with 8% sodium bicarbonate solution (150 ml) and the free base was extracted into ether (3×100 ml). The combined extracts were dried (MgSO$_4$) and evaporated, and the oil was dissolved in ethanol (250 ml) containing 4-(4-fluorophenyl)-2-butanone (3.32 g). The solution was hydrogenated at atmospheric pressure and room temperature over a pre-reduced suspension of 10% palladium oxide on charcoal (0.8 g) and 5% platinum oxide on charcoal (0.8 g) until hydrogen uptake was complete. The catalysts and solvent were removed and the product in ether (200 ml) was converted into its hydrochloride salt (5.96 g), m.p. 144°–146°. Recrystallisation from ethyl acetate-methanol raised the m.p. to 159°–163°.

(b)

$\alpha^1$-[[[3-(4-Fluorophenyl)-1-methylpropyl]amino]methyl]-4-hydroxy-1,3-benzenedimethanol 5-[2-[[3-(4-Fluorophenyl)-1-methylpropyl]amino]-1-hydroxyethyl]-2-hydroxybenzoic acid, methyl ester, hydrochloride (2.66 g) was basified with 8% sodium bicarbonate solution (100 ml) and the free base was extracted into ether (3×100 ml). The dry extracts (MgSO$_4$) were evaporated and the residual oil in tetrahydrofuran (40 ml) was added dropwise under nitrogen to a stirred solution of lithium aluminium hydride (0.74 g) in tetrahydrofuran (40 ml). When the addition was complete, the mixture was stirred at room temperature for 16 hours. The excess hydride was decomposed by the cautious addition of water (10 ml) and then the mixture was evaporated to dryness. The residue was diluted with 2 N hydrochloric acid (100 ml), basified with solid sodium bicarbonate and extracted with ether (2×50 ml). The combined extracts were dried (MgSO$_4$) and diluted with light petroleum (b.p. 60°–80°) until turbid. The product precipitated as an off-white crystalline solid (1.21 g), m.p. 101°–103°. Recrystallization from ether-light petroleum (b.p. 60°–80°) gave colourless needles, m.p. 102°–103°.

EXAMPLE 2

$\alpha^1$-[[[3-(3-Fluorophenyl)-1-methylpropyl]amino]methyl]-4-hydroxy-1,3-benzenedimethanol (a) 5-[2-[[3-(3-Fluorophenyl)-1-methylpropyl]amino]-1-hydroxyethyl]-2-hydroxybenzoic acid, methyl ester, hydrochloride, hemihydrate, m.p. 178°–179° (methanol-ethyl acetate) was prepared as in Example 1(a) using 4-(3-fluorophenyl)-2-butanone.

(b) The free base of the above product 2(a) was reduced with lithium aluminium hydride as described in Example 1(b) to give $\alpha^1$-[[[3-(3-fluorophenyl)-1-methylpropyl]amino]methyl]-4-hydroxy-1,3-benzenedimethanol, m.p. 114°–117° (from ethyl acetate-light petroleum (b.p. 60°–80°)).

EXAMPLE 3

$\alpha^1$-[[[3-(2-Fluorophenyl)-1-methylpropyl]amino]methyl]-4-hydroxy-1,3-benzenedimethanol, hydrochloride, hemihydrate (a) 4-(2-Fluorophenyl)-2-butanone A stirred mixture of 2-fluorobenzyl chloride (22.47 g), acetylacetone (17.10 g), anhydrous potassium carbonate (21.5 g) and ethanol (155 ml) was heated at reflux for 18 hr. The solvent was evaporated and the residue was partitioned between water (200 ml) and ether (150 ml). The aqueous layer was washed with ether (3×150 ml). The extracts were combined, washed with brine (200 ml), dried (MgSO$_4$) and evaporated. Distillation of the residue under reduced pressure gave the product (17 g) b.p. 58°–66°/0.5–0.6 mm.

(b) The above ketone (3a) was used to reductively alkylate 2-hydroxy-5-[[bis(phenylmethyl)amino]acetyl]-benzoic acid, methyl ester as in Example 1(a) to afford 5-[2-[[3-(2-fluorophenyl)-1-methylpropyl]amino]-1-hydroxyethyl]-2-hydroxybenzoic acid, methyl ester, hydrochloride, hemihydrate as a white powder m.p. 135°–141°. Recrystallisation from ethyl acetate-light petroleum (b.p. 60°–80°) gave colourless crystals m.p. 139°–143°.

(c) The free base of the above ester (3b) was treated with lithium aluminium hydride as in Example 1(b) to give $\alpha^1$-[[[3-(2-fluorophenyl)-1-methylpropyl]amino]methyl]-4-hydroxy-1,3-benzenedimethanol, hydrochloride, hemihydrate as a buff powder m.p. 50°–65° (softens).

EXAMPLE 4 erythro-$\alpha^1$-[1-[[3-(4-Fluorophenyl)propyl]amino]ethyl]-4-hydroxy-1,3-benzenedimethanol, hydrochloride, hemihydrate

(a) 3-(4-Fluorophenyl)propanol (i) 5,6-Dihydro-2,4,4,6-tetramethyl-4H-1,3-oxazine (10.98 g) in anhydrous tetrahydrofuran (80 ml) was cooled to −70° under nitrogen. n-Butyllithium in hexane (44 ml) was added dropwise to the stirred solution over approximately 1 hr and the mixture was stirred for a further hour. 4-Fluorobenzyl chloride (12.38 g) in anhydrous tetrahydrofuran (20 ml) was added to the mixture over 30 min and the stirred reaction mixture was allowed to warm to room temperature overnight. The mixture was poured into iced water (100 ml) and adjusted to pH 2–3 with 9 M hydrochloric acid. The solution was extracted with pentane (3×75 ml), then adjusted to pH 14 with 10 M sodium hydroxide, and the resulting oil was extracted with ether (3×75 ml). The solvent was evaporated to give crude 5,6-dihydro-4,4,6-trimethyl-2-[2-(4-fluorophenyl)ethyl]-4H-1,3-oxazine (13.87 g).

(ii) The above crude alkylated dihydro-1,3-oxazine in tetrahydrofuran (80 ml) and absolute ethanol (80 ml) was cooled to −35° and adjusted to pH 7 with 9 M hydrochloric acid. A solution of sodium borohydride (2.48 g) in water (5 ml) was added dropwise to the stirred solution with pH 6–8 maintained by the addition of 9 M hydrochloric acid. The cooled solution was stirred for an additional 1 hr at pH 6–8. The reaction mixture was poured into water (100 ml) and adjusted to pH 14 with 10 M sodium hydroxide. The layers were separated and the aqueous solution was extracted with ether (3×75 ml). The solvent was removed to give the crude tetrahydrooxazine as a yellow oil (12.15 g).

(iii) Steam was passed through a solution of oxalic acid (39.25 g) in water (120 ml) under nitrogen and the above crude tetrahydrooxazine was added dropwise over a period of 20 min. The distillate was extracted with ether (3×75 ml), the extracts were dried (MgSO$_4$) and evaporated to give 3-(4-fluorophenyl)propanol as a colourless oil (4.2 g). The product was purified by short-path distillation.

(b) erythro-5-[2-[[3-(4-Fluorophenyl)propyl]amino]-1-hydroxypropyl]-2-hydroxybenzoic acid, methyl ester, hydrochloride 2-Hydroxy-5-[2-[bis(phenylmethyl)amino]-1-oxopropyl]benzoic acid, methyl ester was generated from the hydrochloride salt (3.4 g) with 8% sodium bicarbonate and extracted into ethyl acetate. A solution of the free base in ethanol (300 ml) was hydrogenated at room temperature and atmospheric pressure over pre-reduced 10% palladium oxide on charcoal (1.0 g) and 5% platinum oxide on charcoal (1.0 g) until hydrogen uptake had ceased.

The catalysts were filtered off and a solution of 3-(4-fluorophenyl)propanol (1.14 g) in ethanol (50 ml) added. The solution was left to stand overnight and was then hydrogenated at room temperature and atmospheric pressure over pre-reduced 10% palladium oxide on charcoal (1.0 g) and 5% platinum oxide on charcoal (1.0 g) until hydrogen uptake had ceased.

The catalysts were filtered off, the solvent was evaporated in vacuo and the residue was dissolved in dry ether. The solution was filtered through "Hyflo" and treated with ethereal hydrogen chloride to give the product as a white solid (1.95 g), m.p. 190°–193° dec. (from methanolethyl acetate).

(c) The free base of the above product (4b) was reduced with lithium aluminium hydride as described in Example 1(b) to give erythro-$\alpha^1$-[1-[[3-(4-fluorophenyl)propyl]amino]ethyl]-4-hydroxy-1,3-benzenedimethanol, hydrochloride, hemihydrate as a colourless powder m.p. 72°–78°.

EXAMPLE 5

$\alpha^1$-[[[3-(4-Fluorophenyl)propyl]amino]methyl]-4-hydroxy-1,3-benzenedimethanol, hemihydrate (a) 2-Hydroxy-5-[[bis(phenylmethyl)amino]acetyl]benzoic acid, methyl ester was reductively alkylated with 3-(4-fluorophenyl)propional as in Example 4(b) to give 5-[2-[[3-(4-fluorophenyl)propyl]amino]-1-hydroxyethyl]-2-hydroxybenzoic acid, methyl ester, hydrochloride as a white powder.

(b) The free base of the above product (5a) was treated with lithium aluminium hydride as described in Example 1(b) to afford $\alpha^1$-[[[3-(4-fluorophenyl)propyl]amino]methyl]-4-hydroxy-1,3-benzenedimethanol, hemihydrate, m.p. 118°–120° (from ether).

EXAMPLE 6

$\alpha^1$-[[[3-(4-Chlorophenyl)-1-methylpropyl]amino]methyl]-4-hydroxy-1,3-benzenedimethanol 4-Hydroxy-$\alpha^1$-[[bis(phenylmethyl)amino]methyl]-1,3-benzenedimethanol (7.0 g) in ethanol (250 ml) and acetic acid (1.2 g) was hydrogenated in the presence of pre-reduced 10% palladium oxide on carbon (0.5 g) and 5% platinum oxide on carbon (0.5 g). Hydrogenation was complete after 25 hr. The catalyst was filtered off, 4-(4-chlorophenyl)-2-butanone (3.52 g) was added and the solution was hydrogenated in the presence of pre-reduced 5% platinum oxide on carbon (1.0 g). Hydrogen uptake was complete in 4.5 hr.

The catalyst and solvent were removed and the residue was basified with sodium bicarbonate (8%) and extracted into ethyl acetate. The solution was dried (MgSO$_4$) and evaporated to give a residue which was crystallised from ethyl acetate/light petroleum (b.p. 60°–80°) (0.6 g) m.p. 99°–103°.

EXAMPLE 7

In a similar manner to that described in Example 6, 4-hydroxy-$\alpha^1$-[[bis(phenylmethyl)amino]methyl]-1,3-benzenedimethanol was reductively alkylated with 4-(3-chlorophenyl)2-butanone to give $\alpha^1$-[[[3-(3-chlorophenyl)-1-methylpropyl]amino]methyl]-4-hydroxy-1,3-benzenedimethanol m.p. 110°–112°. Recrystallisation from chloroform raised the m.p. to 131°–133°.

EXAMPLE 8

4-Hydroxy-$\alpha^1$-[[[3-[4-(dimethylamino)phenyl]-1-methylpropyl]-amino]methyl]-1,3-benzenedimethanol 4-Hydroxy-$\alpha^1$-[[bis(phenylmethyl)amino]methyl]-1,3-benzenedimethanol (5.31 g), 4-[4-(dimethylamino)-phenyl]-2-butanone (2.8 g) and acetic acid (1.75 g) in ethanol (250 ml) were hydrogenated in the presence of 10% palladium oxide on carbon (1.0 g) and 5% platinum oxide on carbon (1.0 g). Hydrogen uptake ceased after 76 hr.

The catalyst and solvent were removed, the residue was basified with sodium bicarbonate (8%) and extracted into ethyl acetate. The solution was dried (MgSO$_4$) and evaporated to give a gummy residue which was crystallised from ether m.p. 132°–135°.

EXAMPLE 9

$\alpha^1$-[[[3-(4-Fluorophenyl)-1-methylpropyl]amino]methyl]-4-hydroxy-1,3-benzenedimethanol 4-Hydroxy-$\alpha^1$-[[bis(phenylmethyl)amino]methyl]-1,3-benzenedimethanol (5.26 g) and 4-(4-fluorophenyl)-2-butanone (2.41 g) in ethanol (350 ml) were hydrogenated at atmospheric pressure and room temperature in the presence of 10% palladium oxide on charcoal (1.0 g) and 5% platinum oxide on charcoal (1.0 g) until hydrogen uptake ceased. The catalysts and solvent were removed and the residual gum was crystallised from ethyl acetate-light petroleum (b.p. 60°–80°), m.p. 98°–105° (3.3 g).

EXAMPLE 10

The following compounds were prepared in a similar manner to that described in Example 9 but replacing 4-(4-fluorophenyl)-2-butanone by the ketone indicated:

(a) 1-(4-Fluorophenyl)-3-pentanone gave $\alpha^1$-[[[3-(4-fluorophenyl)-1-ethylpropyl]amino]methyl]-4-hydroxy-1,3-benzenedimethanol, sulphate (2:1) as a white solid m.p. 104°–110°.

(b) 4-(4-Fluorophenyl)-4-methyl-2-pentanone gave $\alpha^1$-[[[3-(4-fluorophenyl)-1,3,3-trimethylpropyl]amino]-methyl]-4-hydroxy-1,3-benzenedimethanol, hydrochloride as a white solid m.p 105°–110°.

EXAMPLE 11

$\alpha^1$-[[[4-(4-Fluorophenyl)-1-methylbutyl]amino]methyl]-4-hydroxy-1,3-benzenedimethanol (a) 5-(4-Fluorophenyl)-2-pentanol 1-(3-Bromopropyl)-4-fluorobenzene (20 g) in ether (80 ml) was added dropwise to magnesium turnings (2.5 g) in ether (20 ml). The stirred mixture was heated at reflux for 1 hr.

Acetaldehyde (4.06 g) in ether (20 ml) was added dropwise to the mixture at −5°. The stirred mixture was left to warm to room temperature (30 min) and poured onto ice (200 g) and 2 M hydrochloric acid (200 ml). The layers were separated and the aqueous layer was washed with ether (3×150 ml). The combined extracts were dried (MgSO$_4$) and evaporated to give a light yellow liquid (3.95 g) which was purified by chromatography on silica. Light petroleum (b.p. 60°–80°): ethyl acetate (13:7) gave the product as a colourless liquid b.p. 96°–98°/0.4 mm.

(b) 5-(4-Fluorophenyl)-2-pentanone

Chromic acid solution (prepared according to H. C. Brown et al., J. Org. Chem., 1971, 36, 387) (27.5 ml) was added dropwise to a stirred solution of 5-(4-fluorophenyl)-2-pentanol (10 g) in ether (30 ml) such that the temperature did not exceed 30°. The mixture was stirred at room temperature for 2 hr.

The layers were separated. The aqueous layer was washed with ether (2×50 ml). The combined organic extracts were washed with saturated sodium bicarbonate (2×100 ml), brine (1×100 ml), dried (MgSO$_4$) and evaporated to give a yellow oil.

Sodium metabisulphite (11.5 g) in water (25 ml) was added to the crude product in ethanol (100 ml). The precipitated bisulphite-addition compound was filtered off, washed with cold ethanol (100 ml) and then decomposed with 2 M hydrochloric acid (200 ml). The mixture was extracted with ether and the residue remaining after evaporation was distilled b.p. 64°–66°/0.04 mm (8.27 g).

(c) The above ketone (11b) was used to reductively alkylate 4-hydroxy-$\alpha^1$-[[bis(phenylmethyl)amino]methyl]-1,3-benzenedimethanol as described in Example 9 to give $\alpha^1$-[[[4-(4-fluorophenyl)-1-methylbutyl]amino]-methyl]-4-hydroxy-1,3-benzenedimethanol, m.p. 77°–80° (from ether).

EXAMPLE 12

$\alpha^1$-[[[5-(4-Fluorophenyl)-1-methylpentyl]amino]methyl]-4-hydroxy-1,3-benzenedimethanol (a) 6-(4-Fluorophenyl)-3,5-hexadiene-2-one Sodium hydroxide (2 g) in water (35 ml) was added to a stirred mixture of acetone (9.7 g) and ethanol (20 ml) cooled in a water bath. 4-Fluorocinnamaldehyde (5 g) was added dropwise to the stirred solution such that the temperature did not exceed 25°. The mixture was stirred at room temperature for 5 min, diluted with water (250 ml), adjusted to pH 1 with 5 M hydrochloric acid and extracted with ethyl acetate (3×100 ml). The combined extracts were washed with brine (1×100 ml), dried (MgSO$_4$) and evaporated to give an orange oil (6.1 g) which was used crude in the next stage.

(b) 6-(4-Fluorophenyl)-2-hexanone

Crude 6-(4-fluorophenyl)-3,5-hexadien-2-one (6.1 g) in ethanol (200 ml) was hydrogenated at room temperature and atmospheric pressure over pre-reduced 10% palladium oxide on charcoal (1.0 g). Hydrogen uptake was complete in 1.5 hr. The catalyst and solvent were removed to give a yellow oil (5.8 g) which was dissolved in ethanol (60 ml) and treated with sodium metabisulphite (5.67 g) in water (15 ml). The precipitated bisulphite addition compound was filtered off, washed with ethanol and then decomposed with 2 M hydrochloric acid (150 ml). The mixture was extracted with ethyl acetate to give a light yellow oil (2.56 g). Short-path distillation gave a colourless oil (2.3 g) b.p. 80°/0.06 mm.

(c) Using the method described in Example 9, 4-hydroxy-$\alpha^1$-[[bis(phenylmethyl)amino]methyl]-1,3-benzenedimethanol was reductively alkylated with 6-(4-fluorophenyl)-2-hexanone to give $\alpha^1$-[[[5-(4-fluorophenyl)-1-methylpentyl]amino]methyl]4-hydroxy-1,3-benzenedimethanol m.p. 72°–77° (from ether).

EXAMPLE 13

α¹-[[[3-[4-(Trifluoromethyl)phenyl]-1-methylpropyl]amino]methyl]-4-hydroxy-1,3-benzenedimethanol

(a) 1-(Chloromethyl)-4-(trifluoromethyl)benzene

Thionyl chloride (15.0 g) was added to 4-(trifluoromethyl)benzenemethanol (15.0 g) over 30 min. The mixture was heated at reflux for 2 hr and then evaporated. The residue was distilled to afford the product as a colourless liquid b.p. 88°–92°/14 mm (11.0 g).

(b) 4-(4-Trifluoromethyl)phenyl-2-butanone

A stirred mixture of 1-(chloromethyl)-4-(trifluoromethyl)benzene (8.0 g), acetylacetone (4.1 g) and anhydrous potassium carbonate (6.9 g) in dry ethanol (50 ml) was heated at reflux for 22 hr. The solvent was removed and the residue was distilled. The fraction b.p. 74°–78°/0.6 mm (2.7 g) contained the required product contaminated with 18% 4-(trifluoromethyl)benzenemethanol. A solution of the impure ketone (2.7 g) in ethanol (27 ml) was added to a solution of sodium metabisulphite (2.4 g) in water (9 ml). The gelatinous precipitate was filtered off and decomposed with 2 M aqueous hydrochloric acid (30 ml). The mixture was extracted with ether, dried (MgSO₄) and evaporated to afford the pure ketone (1.7 g) as a colourless oil.

(c) The above ketone (13b) was used to reductively alkylate α¹-[[bis(phenylmethyl)amino]methyl]-1,3-benzenedimethanol by the method described in Example 9, to afford α¹-[[[3-[4-(trifluoromethyl)phenyl]-1-methylpropyl]amino]methyl]-4-hydroxy-1,3-benzenedimethanol, m.p. 101°–103° (ether).

EXAMPLE 14

α¹-[[[3-(4-Fluorophenyl)-2,2-dimethylpropyl]amino]methyl]-4-hydroxy-1,3-benzenedimethanol, hydrochloride, hemihydrate

(a) 3-(4-Fluorophenyl)-2,2-dimethyl-1-propanal

A mixture of sodium hydroxide (4.2 g), water (4.2 g), benzene (6 ml) and tetrabutylammonium iodide (0.45 g) was heated to 70°. A solution of isobutyraldehyde (8.65 g) and 4-fluorobenzyl chloride (13.01 g) was dripped into the mixture which was stirred at 70° for 5 hr. The product was extracted into ether, the solution was dried (MgSO₄) and evaporated to give an oil b.p. 80°/1.0 mm (15.30 g).

(b) α¹-[[[3-(4-Fluorophenyl)-2,2-dimethylpropyl]amino]methyl]4-hydroxy-1,3-benzenedimethanol, hydrochloride, hemihydrate 4-Hydroxy-α¹-[[bis(phenylmethyl)amino]methyl]-1,3-benzenedimethanol (5.0 g) in ethanol (150 ml) was hydrogenated in the presence of pre-reduced 10% palladium oxide on carbon (0.5 g) and 5% platinum oxide on carbon (0.5 g). Hydrogen uptake was complete within 68 hr. The catalyst was filtered off and the solution was refluxed with 3-(4-fluorophenyl)-2,2-dimethyl-1-propanal (3.88 g) for 2 hr. After cooling the solution was hydrogenated in the presence of pre-reduced 10% palladium oxide on carbon (0.5 g). Hydrogen uptake ceased after 15 hr. Catalyst and solvent were removed to give a gum which was dissolved in methanol and treated with ethereal hydrogen chloride. The methanol was evaporated off in vacuo to give a foam which was triturated under dry ether to give a buff powder (4.21 g) m.p. 50° (softens).

EXAMPLE 15

α¹-[[[3-(4-Fluorophenyl)-1,1-dimethylpropyl]amino]methyl]-4-hydroxy-1,3-benzenedimethanol, hydrochloride, hemihydrate

(a) 5-(Dichloroacetyl)-2-(phenylmethoxy)benzoic acid, methyl ester

Chlorine gas was slowly bubbled through a stirred solution of 5-acetyl-2-(phenylmethoxy)benzoic acid, methyl ester (20 g) in acetic acid (350 ml) at 60°–65° until the solution was pale yellow (ca. 5 hr.). The solution was purged with nitrogen to remove the excess of chlorine and then evaporated. The colourless crystalline product was recrystallised from ethyl acetate-light petroleum (b.p. 60°–80°) as colourless platelets m.p. 132°–134° (17.03 g).

(b) 5-(Oxoacetyl)-2-(phenylmethoxy)benzoic acid, methyl ester, hydrate 5-(Dichloroacetyl)-2-(phenylmethoxy)benzoic acid, methyl ester (2.4 g) was added to sodium (0.34 g) in dry methanol (80 ml). The solution was boiled for 20 min. 0.1 N Hydrochloric acid (40 ml) was added and the solution was boiled for 30 min. The methanol was evaporated off and the mixture was extracted with ether (3×50 ml). The extracts were dried (MgSO₄) and evaporated to leave crude 5-(oxoacetyl)-2-(phenylmethoxy)benzoic acid, methyl ester, hydrate as a gum.

(c) 4-(4-Fluorophenyl)-2-methyl-2-butanamine, hydrochloride

(i) 4-(4-Fluorophenyl)-2-methyl-2-butanol 4-(4-Fluorophenyl)-2-butanone (10.0 g) in ether (30 ml) was added over 20 min. to a stirred solution of methyl magnesium iodide (0.086 mole) in ether (80 ml). The mixture was stirred at room temperature over 5 hr, then cooled and 2 M sulphuric acid (30 ml) added. The mixture was extracted with ether (5×50 ml), washed with saturated sodium bicarbonate solution, saturated brine and dried (MgSO₄). The solvent was removed and the residue was distilled. The alcohol (9.4 g) b.p. 83°–85°/0.1 mm was obtained as a colourless liquid.

(ii) 4-(4-Fluorophenyl)-2-methyl-2-butanamine, hydrochloride

Sulphuric acid (d. 1.84, 18 ml) was added dropwise over 10 min. to an ice-cold stirred suspension of potassium cyanide (9.5 g) and 4-(4-fluorophenyl)-2-methyl-2-butanol (10.0 g) in chloroform (80 ml). The mixture was allowed to warm to room temperature and was stirred over 20 hr. The mixture was basified with 5 N sodium hydroxide solution and was extracted with chloroform. The solvent was removed to leave a pale yellow oil which was treated with hydrochloric acid (d. 1.18, 30 ml) at reflux for 1 hr. The product (9.0 g) crystallised from the acid solution as colourless plates, m.p. 200°–201°.

(d) α¹-[[[3-(4-Fluorophenyl)-1,1-dimethylpropyl]amino]methyl]-4-(phenylmethoxy)-1,3-benzenedimethanol Crude 5-(oxoacetyl)-2-(phenylmethoxy)benzoic acid, methyl ester, hydrate (prepared in 15b above) in ethanol (100 ml) was treated with 4-(4-fluorophenyl)-2-methyl- 2-butanamine (generated from its hydrochloride salt (1.5 g) prepared in (c) above). The solution was boiled for 30 min. and then evaporated to leave a yellow gum. The gum in dry tetrahydrofuran (50 ml) was dripped into a stirred solution of lithium aluminium hydride (1.0 g) in dry tetrahydrofuran (50 ml) at room temperature. The mixture was stirred for 20 hr. then boiled for 2 hr. Water (5 ml) was slowly added, the mixture was filtered and the filtrate was evaporated to leave a colourless gum which crystallised from ether-light petroleum (b.p. 60°–80°) as colourless needles, m.p. 76°–79° (0.37 g).

(e)
$\alpha^1$-[[[3-(4-Fluorophenyl)-1,1-dimethylpropyl]amino]-methyl]-4-hydroxy-1,3-benzenedimethanol, hydrochloride, hemihydrate $\alpha^1$-[[[3-(4-Fluorophenyl-1,1-dimethylpropyl]amino]-methyl]-4-(phenylmethoxy)-1,3-benzenedimethanol (1.86 g) in ethanol (100 ml) was added to pre-reduced 10% palladium oxide on charcoal (0.35 g) in ethanol (30 ml). The stirred mixture was treated with hydrogen at atmospheric pressure and room temperature until uptake ceased. The catalyst and solvent were removed and the resultant oil was converted into its hydrochloride in ether. The gummy salt was solidified by trituration under ether (0.95 g) m.p. 114°–119°.

EXAMPLE 16

(a)
$\alpha^1$-[[[3-[4-(Acetylamino)phenyl]-1-methylpropyl]amino]methyl]-4-hydroxy-1,3-benzenedimethanol, hemihydrate 4-Hydroxy-$\alpha^1$-[[bis(phenylmethyl)amino]methyl-]-1,3-benzenedimethanol (5.0 g) and N-[4-(3-oxobutyl)-phenyl]acetamide (2.82 g) in ethanol (200 ml) were hydrogenated in the presence of pre-reduced 10% palladium oxide on carbon (1.0 g) and 5% platinum oxide on carbon (1.0 g). Hydrogen uptake was complete after 43 hr. Catalyst and solvent were removed to give a glass which was triturated under dry ether to give a cream solid (4.53 g).

(b)
$\alpha^1$-[[[3-[4-(Ethylamino)phenyl]-1-methylpropyl]amino]methyl]-4-hydroxy-1,3-benzenedimethanol, dihydrochloride, hemihydrate $\alpha^1$-[[[3-[4-(Acetylamino)phenyl]-1-methylpropyl]amino]methyl]-4-hydroxy-1,3-benzenedimethanol, hemihydrate (3.38 g) in dry tetrahydrofuran (100 ml) was dripped into a solution of lithium aluminium hydride (1.0 g) in dry tetrahydrofuran (50 ml). The mixture was boiled for 43 hr. The excess of lithium aluminium hydride was destroyed with ethyl acetate and the solvent removed. The residue was acidified with 5 N hydrochloric acid, basified with sodium bicarbonate and extracted with chloroform. The chloroform was evaporated off to give a gum which was dissolved in methanol and treated with ethereal hydrogen chloride. The solvent was removed and the resulting gum was triturated under dry ether to give a buff solid (1.44 g) m.p. 107°–110°.

EXAMPLE 17

| Pharmaceutical Compositions | |
|---|---|
| Tablets | per tablet |
| Active compound* (sieved through 60 mesh) | 2 mg |

-continued

| Pharmaceutical Compositions | |
|---|---|
| Tablets | per tablet |
| Spray dried calcium phosphate dihydrate | 176 mg |
| Sta-Rx 1500** | 20 mg |
| Magnesium stearate | 2 mg |

*The active compound in these composition is the compound of Examples 1 and 9.
**A free-flowing compressible form of starch.

The powders are intimately mixed and compressed into tablets.

| Inhalation aerosols | dose in each can |
|---|---|
| Active compound (micronised) | 24 mg |
| Sorbitan trioleate | 2.4 mg |
| trichlorofluoromethane | 5.7 g |
| dichlorodifluoromethane | to 20.4 g |

A suspension of the finely powdered drug is dispersed in the trichlorofluoromethane containing the sorbitan trioleate. The required quantity of this suspension is metered into each can, a metering valve is crimped on to each can and the dichlorodifluoromethane is metered into each can be pressure-filling through the valve. The valve delivers 85 mg of total suspension in each metered dose, containing 100 μg of the drug.

| Inhalation capsules | per capsule |
|---|---|
| Active compound (micronised) | 200/μg |
| lactose BP. | 25 mg |

The drug and lactose are intimately mixed and the mix is filled into hard gelatin capsules. The capsules are used in a suitable insufflator which delivers a finely dispersed powder cloud to the patients lungs via the mouth.

| Injection solution | per 5 ml ampoule |
|---|---|
| Active compound | 0.50 mg |
| Hydrochloric acid | q.s. to give pH 4.5 |
| Water for Injections BP | to 5 ml |

The solution is sterilised by membrane filtration and filled into sterilised ampoule.

The active compound used in the above formulations may be replaced by any compound according to the invention if desired.

We claim:

1. Compounds of the formula

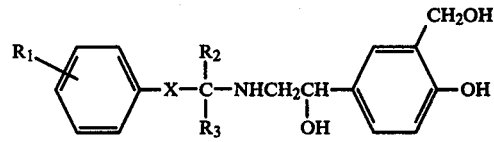

wherein $R_1$ represents fluorine, chlorine or dimethylamino, X represents $(CH_2)_n$ where n is 2 or 3, $R_2$ and $R_3$ are hydrogen or methyl.

2. Compounds as claimed in claim 1 in which the group represented by the formula:

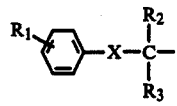

is selected from the group consisting of:
3-(4-fluorophenyl)-1-methylpropyl,
3-(4-chlorophenyl)-1-methylpropyl,
3-(4-dimethylaminophenyl)-1-methylpropyl,
3-(2-fluorophenyl)-1-methylpropyl,
3-(3-fluorophenyl)-1-methylpropyl,
3-(4-fluorophenyl)propyl,
3-(4-fluorophenyl)-1,1-dimethylpropyl, and
4-(4-fluorophenyl)-1-methylbutyl.

3. Compounds as claimed in claim 1 in which $R_1$ represents a fluorine or chlorine atom.

4. Compounds as claimed in claim 1 in which at least one of $R_2$ and $R_3$ represents a methyl group.

5. A compound of claim 1 which is $\alpha^1$-[[[3-(4-fluorophenyl)-1-methylpropyl]amino]methyl]-4-hydroxy-1,3-benzenedimethanol.

6. A compound of claim 1 which is $\alpha^1$-[[[3-(3-fluorophenyl)-1-methylpropyl]amino]methyl]-4-hydroxy-1,3-benzenedimethanol.

7. A compound of claim 1 which is erythro-$\alpha^1$-[1-[[3-(4-fluorophenyl)propyl]amino]ethyl]-4-hydroxy-1,3-benzenedimethanol.

8. A compound of claim 1 which is $\alpha^1$-[[[3-(4-fluorophenyl)propyl]amino]methyl]-4-hydroxy-1,3-benzenedimethanol.

9. A compound of claim 1 which is $\alpha^1$-[[[3-(4-chlorophenyl)-1-methylpropyl]amino]methyl]-4-hydroxy-1,3-benzenedimethanol.

10. A compound of claim 1 which is $\alpha^1$-[[[3-(3-chlorophenyl)-1-methylpropyl]amino]methyl]-4-hydroxy-1,3-benzenedimethanol.

11. A compound of claim 1 which is 4-hydroxy-$\alpha^1$-[[[3-(4-(dimethylamino)phenyl]-1-methylpropyl]amino]methyl]-1,3-benzenedimethanol.

12. A compound of claim 1 which is $\alpha^1$-[[[3-(4-fluorophenyl)-1-ethylpropyl]amino]methyl]-4-hydroxy-1,3-benzenedimethanol.

13. A compound of claim 1 which is $\alpha^1$-[[[3-(4-fluorophenyl)1,3,3-trimethylpropyl]amino]methyl]-4-hydroxy-1,3-benzenedimethanol.

14. A compound of claim 1 which is $\alpha^1$[[[4-(4-fluorophenyl)-1-methylbutyl]amino]methyl]-4-hydroxy-1,3-benzenedimethanol.

15. A compound of claim 1 which is $\alpha^1$-[[[5-(4-fluorophenyl)-1-methylpentyl]amino]methyl]-4-hydroxy-1,3-benzenedimethanol.

16. A compound of claim 1 which is $\alpha^1$-[[[3-(4-fluorophenyl)-2,2-dimethylpropyl]amino]methyl]-4-hydroxy-1,3-benzenedimethanol.

17. A compound of claim 1 which is $\alpha^1$-[[[3-(4-fluorophenyl)-1,1-dimethylpropyl]amino]methyl]-4-hydroxy-1,3-benzenedimethanol.

18. A pharmaceutical composition comprising a compound as claimed in claim 1 in association with an inert pharmaceutically acceptable carrier or diluent.

19. Compositions as claimed in claim 18 adapted for oral use and in the form of tablets.

20. Compositions as claimed in claim 19 in dosage unit form each dosage unit containing up to 100 mg of active ingredient.

21. A composition as claimed in claim 18 adapted for administration by inhalation and in the form of a metered dose inhalation aerosol, a solution or suspension suitable for nebulisation by mechanical means, or as a cartridge from which the powdered composition may be inhaled with the aid of a suitable device.

22. A composition as claimed in claim 21 in which the metered dose is from 50–1000 $\mu$g.

23. A method for the treatment of a patient to relieve bronchospasm which comprises administering an effective amount of a compound as claimed in claim 1.

* * * * *